US00PP08725P

United States Patent [19]

Schumann

[11] Patent Number: Plant 8,725

[45] Date of Patent: May 10, 1994

[54] GERANIUM PLANT NAME FISMAG

[75] Inventor: Ingeborg Schumann, Albstadt, Fed. Rep. of Germany

[73] Assignee: Florfis AG, Binningen, Switzerland

[21] Appl. No.: 94,325

[22] Filed: Jul. 21, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Foley & Lardner

[57] ABSTRACT

A new and distinct cultivar of geranium named Fismag, particularly characterized by the combined features of cherry red semi-double flowers, medium green foliage with slight zonation, medium growth habit, and medium to early flower response.

1 Drawing Sheet

1

The present invention comprises a new and distinct cultivar of geranium, botanically known as *Pelargonium zonale l'hert*, and hereinafter referred to by the cultivar name Fismag.

Fismag is a product of planned breeding program which had the objective of creating new geranium cultivars with cherry red flower color, foliage with zonation, and medium growth habit.

Fismag was originated from a hybridization made by inventor Ingeborg Schumann in a controlled breeding program in Galdar, Gran Canaria, Spain in 1987. The female parent was an unnamed hybrid derived from a cross between a self seedling of the cultivars Rospen and Twist, the latter being disclosed in U.S. Plant Pat. No. 5,928. Rospen is characterized by purple rose flowers with eyes on petals and leaves with medium zonation. Twist has salmon rose flowers, dark green foliage, and compact habit. The male parent of Fismag was the result of the selfing of a hybrid obtained by crossing a self seedling of Purlapen with a self seedling of Dresden Doll Pink Purlapen, disclosed in U.S. Plant Pat. No. 5,054 under the vertical name Veronika, is characterized by red purple flower color and foliage with weak zonation. Dresden Doll Pink has single pink flowers with purple eyes and leaves without zonation.

Fismag was discovered and selected as one flowering plant within the progeny of the stated cross by Ingeborg Schumann in 1988 in a controlled environment in Galdar, Gran Canaria, Spain.

The first act of asexual reproduction of Fismag was accomplished when vegetative cuttings were taken from the initial selection in February 1989 in a controlled environment in Galdar, Gran Canaria, Spain, by, or under the supervision of, Ingeborg Schumann.

Horticultural examination of plants grown from these cuttings initiated in May 1989, in Hillscheid, Federal Republic of Germany, and continuing thereafter, has demonstrated that the combination of characteristics as herein disclosed for Fismag are firmly fixed and are retained through successive generations of asexual reproduction.

Fismag has not been observed under all possible environmental conditions. The phenotype may vary significantly with variations in environment such as temperature, light intensity and day length without, however, any variation in genotype. The following observations, measurements, and comparisons describe plants grown in Hillscheid, Federal Republic of Germany under

2 greenhouse conditions which approximate those generally used in commercial practice.

The following traits have been repeatedly observed and are determined to be basic characteristic of Fismag, which in combination distinguish this geranium as a new and distinct cultivar:

1. Cherry red flower color
2. Weak salmon red coloring at the base of upper petals
3. Semi-double flower type
4. Medium green foliage with slight zonation
5. Medium growth habit
6. Medium to early flower response Of the many commercial cultivars known to the present inventor, the most similar in comparison to Fismag is the patented variety Disco, disclosed in U.S. Plant Pat. No. 5,930. Reference is made to attached Chart A which compares certain characteristics of Fismag to those same characteristics of Disco. In general comparison to Disco, Fismag has a more bluish shade of flower color, deeper green foliage with slight zonation, and a somewhat more vigorous growth.

The accompanying color photographic drawing shows typical flower and foliage characteristics of Fismag, with colors being as true as possible with illustrations of this type.

In the following description color references are made to The Royal Horticultural Society Color Chart. The color values were determined indoors from plants grown in the greenhouse in May 1993 at Hillscheid, Federal Republic of Germany.

Classification:

*Botanical.*—A hybrid of the species *Pelargonium zonale l'Hert.*

*Commercial.*—Zonal geranium, cv., Fismag.

INFLORESCENCE

A. Umbel:

*Shape.*—Semi-spherical.

*Average diameter.*—100 mm.

*Average depth.*—65 mm.

*Peduncle length.*—167 mm.

*Pedicel length.*—22 mm.

*Pedicel color.*—*Upper part dark red, approximately* 185 A.

*Number of flowers per umbel.*—50–60.

B. Corolla:

*Average diameter.*—46 mm.

*Form.*—Semi-double.

*Number of petals.*—6–8.

*Number of petaloids.*—1–3.

*Color (general tonality from a distance of three meters).*—Cherry red.

*Color of upper petals.*—Between 45B and 57B. Salmon red 43A spot at the base.

*Color of lower petals.*—57B.

*Markings.*—No markings.

*Color of lower surface of petals.*—Between 52A and 58C.

*Number of sepals.*—5.

*Color of sepals.*—Mainly dark red.

C. Bud:

*Shape.*—Round to elliptic.

*Color (adaxial).*—Green, with anthocyanine at the base.

*Color (abaxial).*—Bluish pink to cherry red.

D. Reproductive organs:

*Androecium.*—7–9 fertile anthers, white filament, orange pollen

*Gynoecium.*—5–6 lobed stigma, red style and stigma

E. Spring flowering response period: In Hillscheid, Federal Republic of Germany, in 1993 plants had on average 0.8 flowers opened 10 weeks after planting of unrooted cuttings.

F. Outdoor flower production: The flower count in 1992 in Hillscheid, Federal Republic of Germany was between 25 and 30 flowers per plant for May through September observation period.

G. Durability: Good shatter resistance.

PLANT

A. Foliage:

*Form.*—Kidney-shaped.

*Margin.*—Bicrenated.

*Size of leaf.*—95–100 mm.

*Color of upper surface.*—Medium green, approximately 137C.

*Color of zonation.*—Dark green, approximately between 137A and 147A.

*Tolerance of botrytis.*—Average.

B. General appearance and form:

*Internode length.*—15–20 mm.

*Branching pattern.*—3.15 branches per week.

*Height (12 week old plants).*—15 cm.

CHART A

| CHARACTERISTICS | FISMAG | DISCO |
|---|---|---|
| Flower color | 57 B | 45 B |
| Markings on upper petals | Weak salmon red 43 A, spot at base | Red purple eye, 57 A |
| Color of leaf | 137 C | 137 D |
| Zonation | Weak zonation | No zonation |
| Height | 15 cm | 12 cm |
| Internodes | 30–45 mm | 15–35 mm |

I claim:

1. A new and distinct cultivar of geranium plant named Fismag, as illustrated and described.

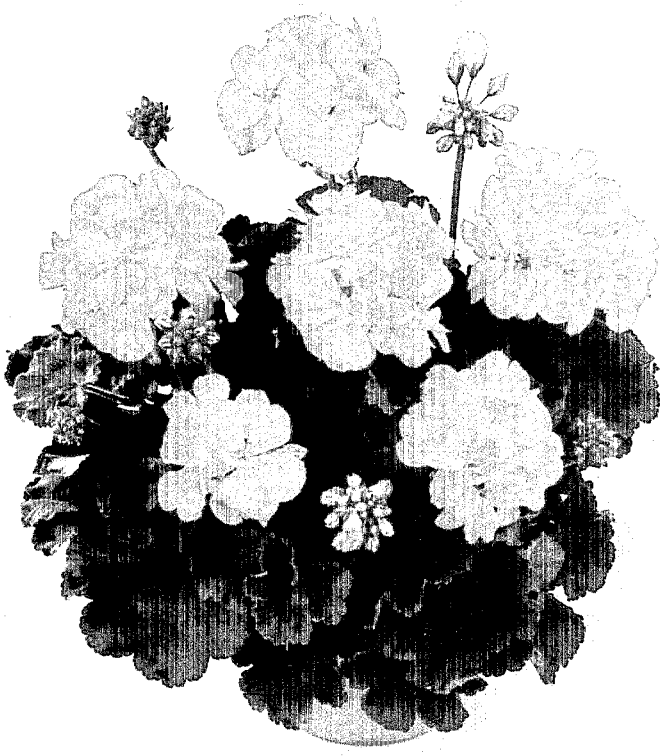

* * * * *